(12) United States Patent
Ogawa

(10) Patent No.: US 7,495,779 B2
(45) Date of Patent: Feb. 24, 2009

(54) LEVEL DETECTION APPARATUS

(75) Inventor: Riki Ogawa, Kanagawa (JP)

(73) Assignee: Advanced Mask Inspection Technology, Inc., Yokohama-shi (JP)

( * ) Notice: Subject to any disclaimer, the term of this patent is extended or adjusted under 35 U.S.C. 154(b) by 0 days.

(21) Appl. No.: 12/031,223

(22) Filed: Feb. 14, 2008

(65) Prior Publication Data

US 2008/0231846 A1 Sep. 25, 2008

(30) Foreign Application Priority Data

Mar. 19, 2007 (JP) ............................. 2007-070397

(51) Int. Cl.
*G01B 11/00* (2006.01)
*G01B 11/14* (2006.01)
*G02B 27/40* (2006.01)

(52) U.S. Cl. .................. 356/614; 356/609; 356/620; 356/624; 250/201.4; 250/548

(58) Field of Classification Search ......... 356/601–624, 356/399–400; 250/201.3, 201.4, 548, 559.22
See application file for complete search history.

(56) References Cited

U.S. PATENT DOCUMENTS

| | | | | |
|---|---|---|---|---|
| 4,400,070 A | * | 8/1983 | Isono et al. ................. 351/208 |
| 4,748,333 A | * | 5/1988 | Mizutani et al. ........ 250/559.07 |
| 5,218,415 A | * | 6/1993 | Kawashima .............. 356/139.1 |
| 5,587,794 A | * | 12/1996 | Mizutani et al. ............. 356/623 |
| 5,955,739 A | * | 9/1999 | Kawashima ................. 250/548 |
| 6,124,933 A | * | 9/2000 | Mizutani et al. ............. 356/620 |
| 7,071,451 B2 | * | 7/2006 | Ishikawa et al. ........... 250/201.4 |

FOREIGN PATENT DOCUMENTS

JP 5-297262 11/1993

* cited by examiner

*Primary Examiner*—Sang Nguyen
(74) *Attorney, Agent, or Firm*—Oblon, Spivak, McClelland, Maier & Neustadt, P.C.

(57) ABSTRACT

A level detection apparatus includes an illumination slit in which a rectangular first opening which causes illumination light to pass is formed, an optical system configured to illuminate a target object surface by illumination light passing through the illumination slit and focuses reflected light from the target object surface, first and second detection slits which are arranged in front of and in back of a focal point and in each of which a second opening is formed such that a short side of a rectangle is shorter than a short side of a illumination slit image formed by the illumination slit and a long side of the rectangle is larger than a long side of the illumination slit image, first and second light amount sensors configured to detect amounts of light of the reflected lights passing through the first and second detection slits, and a calculating unit configured to calculate a level of the target object surface based on outputs from the first and second light amount sensors.

10 Claims, 9 Drawing Sheets

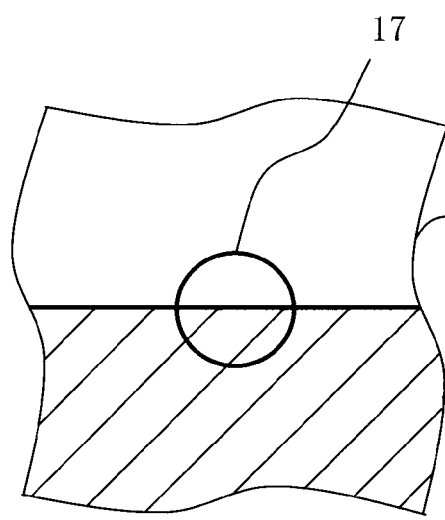
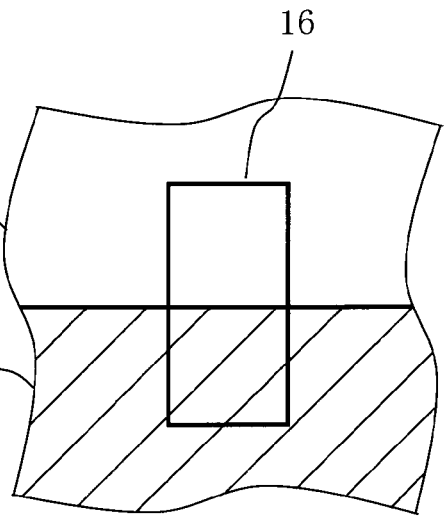
FIG. 4A    FIG. 4B
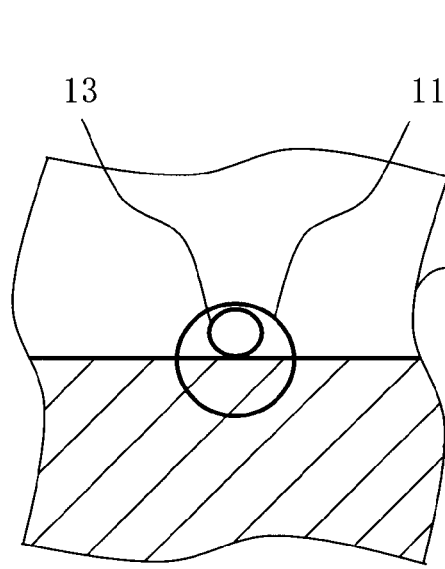
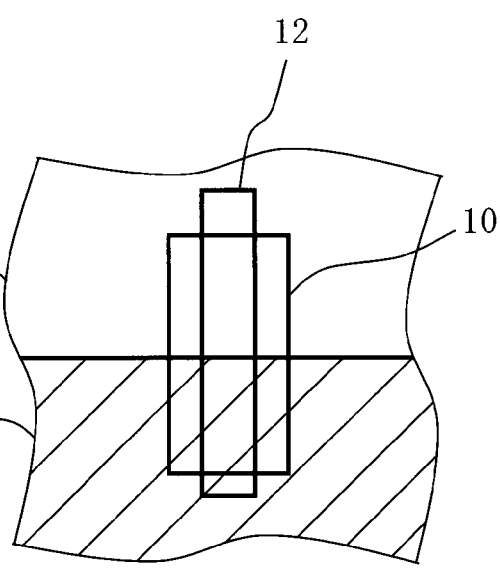
FIG. 5A    FIG. 5B

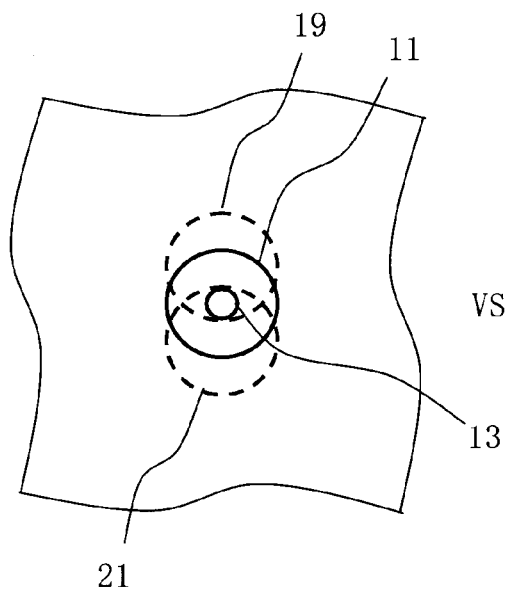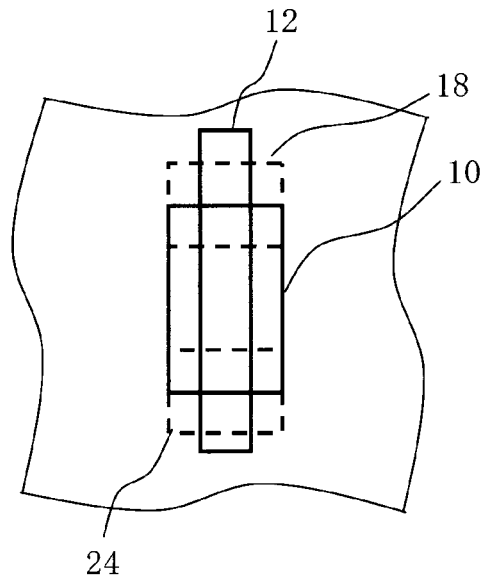
FIG. 8A  FIG. 8B
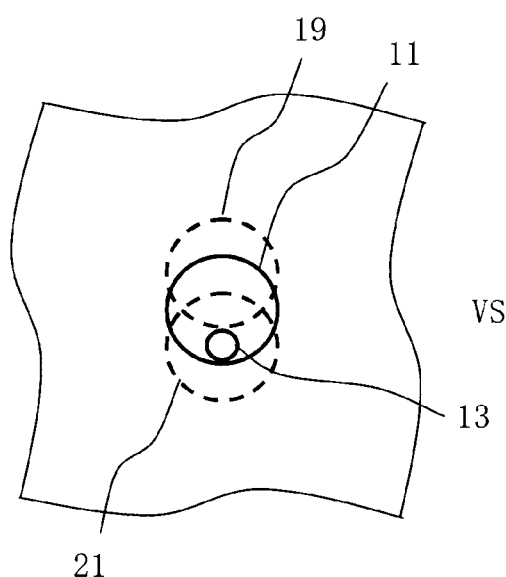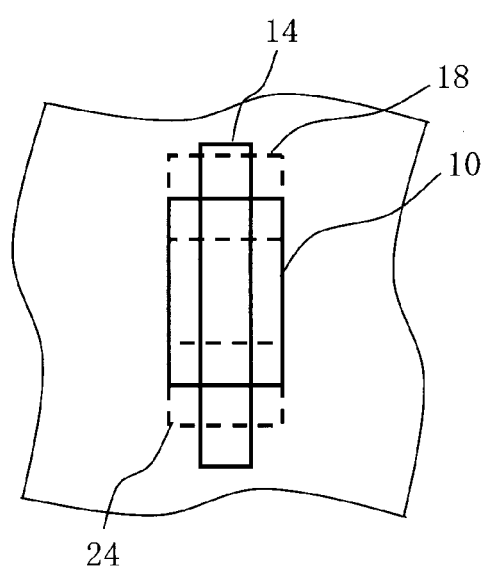
FIG. 9A  FIG. 9B

LEVEL DETECTION APPARATUS

CROSS-REFERENCE TO RELATED APPLICATION

This application is based upon and claims the benefit of priority from prior Japanese Patent Application No. 2007-070397 filed on Mar. 19, 2007 in Japan, the entire contents of which are incorporated herein by reference.

BACKGROUND OF THE INVENTION

1. Field of the Invention

The present invention relates to a level detection apparatus, for example an auto-focus technique of a pattern inspection apparatus which inspects a pattern defect of an object serving as a sample used in semiconductor manufacturing. The present invention also relates to an auto-focus technique of a pattern inspection apparatus to inspect a defect of a lithography mask used when a semiconductor device or a liquid crystal display (LCD) is manufactured.

2. Related Art

In order to irradiate light on a surface of an object to measure a level of a target object surface from the reflected light from the surface, the following technique is used as a conventional method. Light from a light source is converged to form a beam spot on the target object. A circular pin hole which focuses the reflected light and splits a beam of light in front of a focal point to regulate one of the beams of light in front of the focal point is installed, and a circular pin hole to regulate the other of the beams of light in back of the focal point is installed. Amounts of lights passing through the circular pin holes are detected by separate sensors, respectively. A level of the target object is detected on the basis of a ratio of the amounts of light (for example, see Japanese Patent Application, Publication No. JP-A-05-297262).

However, this method has the following problems. First, an amount of light is insufficient in an optical system such as a Koehler illumination system in which a point source cannot be easily formed.

Secondly, when an image obtained from a target object crosses a boundary of different reflection distributions of the target object, an error easily occurs due to the reflectance distribution of the object. The problem can be avoided when the optical positions of the circular pin holes installed in front of or in back of the focal point completely coincide with each other. However, when the positions are different from each other in installation of the circular pin holes, a large amount of light may enter into one of the circular pin holes, and only a relatively small amount of light may enter the other pin hole. In this case, since light amounts cannot be accurately detected, a detected level position of the target object has an error. However, it is difficult to cause the optical positions of the two circuit pin holes to completely coincide with each other. When the circular pin holes are used, the detection is disadvantageously influenced by the reflectance distribution.

Thirdly, when diffracted light caused by a pattern of a target object is generated, an error is easily generated by the influence of the diffracted light. This can be avoided when the optical positions of circular pin holes installed in front of and in back of a focal point. However, when the positions are different from each other in the installation of the pin holes, a large amount of diffracted light may enter into one of the circular pin holes, and only a relatively small amount of light may enter into the other circular pin hole. In this case, since the amounts of light cannot be accurately detected, a detected level position of the target object has an error. However, as described above, it is difficult to cause the optical positions of the two circuit pin holes to completely coincide with each other. When the circular pin holes are used, the detection is disadvantageously influenced by the diffracted light generated by a periodic pattern of the target object.

BRIEF SUMMARY OF THE INVENTION

A level detection apparatus according to an aspect of the present invention includes an illumination slit in which a rectangular first opening which causes illumination light to pass is formed, an optical system configured to illuminate a target object surface by illumination light passing through the illumination slit and focuses reflected light from the target object surface, first and second detection slits which are arranged in front of and in back of a focal point and in each of which a second opening is formed such that a short side of a rectangle is shorter than a short side of a illumination slit image formed by the illumination slit and a long side of the rectangle is larger than a long side of the illumination slit image, first and second light amount sensors configured to detect amounts of light of the reflected lights passing through the first and second detection slits, and a calculating unit configured to calculate a level of the target object surface based on outputs from the first and second light amount sensors.

BRIEF DESCRIPTION OF THE DRAWINGS

FIGS. 4A and 4B are diagrams showing an example obtained by comparing a circular pin hole and a rectangular slit when a target object surface having a reflectance distribution is illuminated;

FIGS. 5A and 5B are diagrams showing an example obtained by comparing a case in which an illumination image in front of a focal point of a target object surface having a reflectance distribution passes through the circular pin hole with a case in which the illumination image passes through the rectangular slit;

FIGS. 8A and 8B are diagrams showing an example obtained by comparing a case in which an illumination image in front of a focal point of the target object surface having the striped pattern passes through the circular pin hole with a case in which the illumination image passes through the rectangular slit;

FIGS. 9A and 9B are diagrams showing an example obtained by comparing a case in which an illumination image in back of the focal point of the target object surface having the striped pattern passes through the circular pin hole with a case in which the illumination image passes through the rectangular slit;

DETAILED DESCRIPTION OF THE INVENTION

First Embodiment

Figure 1:
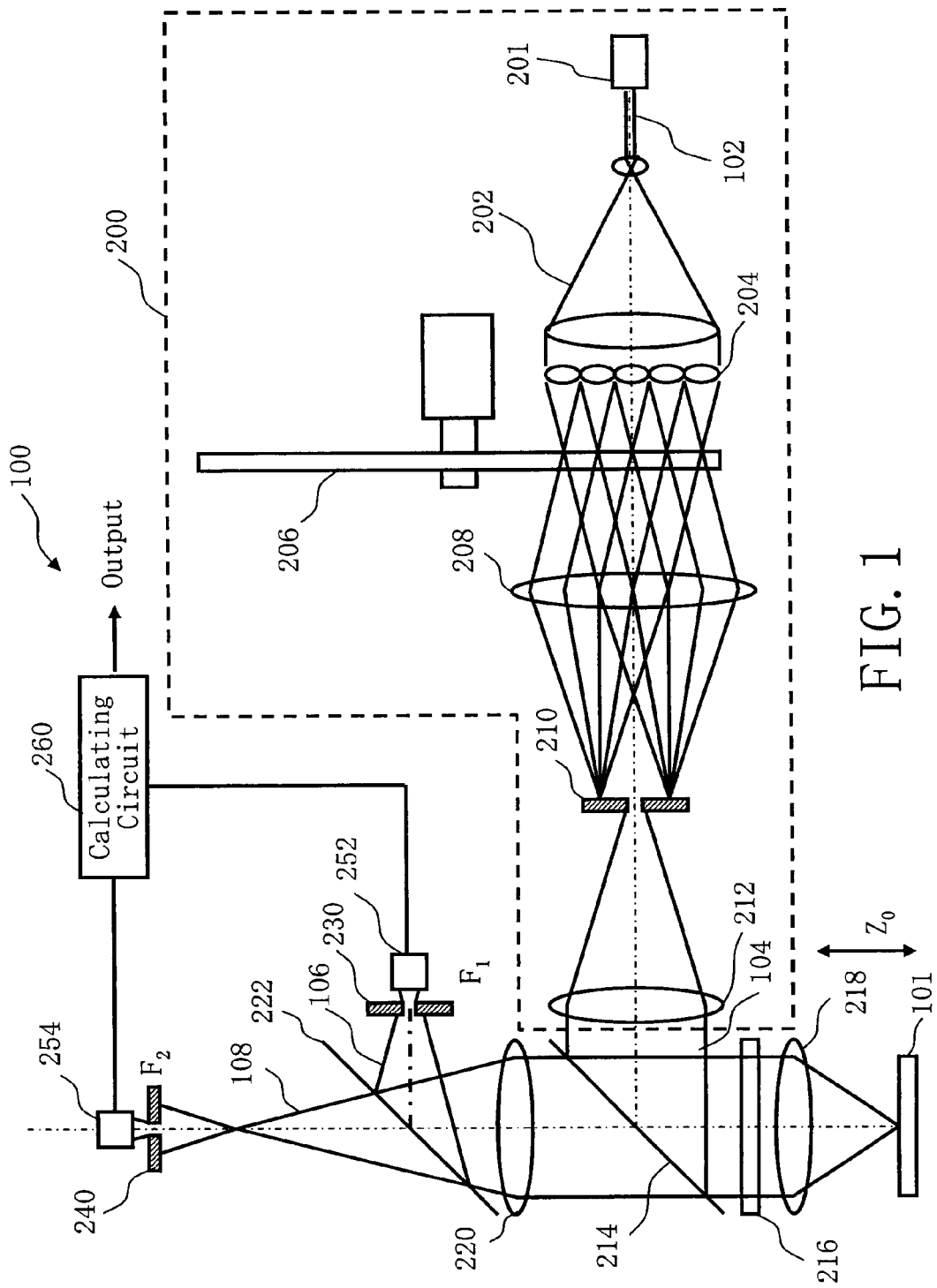
FIG. 1 is a conceptual diagram showing a configuration of a level detection apparatus according to a first embodiment.

FIG. 1 is a conceptual diagram showing a configuration of a level detection apparatus according to a first embodiment.

In FIG. 1, a level detection apparatus 100 has an illumination optical system 200, a polarizing beam splitter 214, a ¼ wavelength plate $\lambda X/4$ plate) 216, an objective lens 218, a focusing lens 220, a beam splitter 222, an illumination slit 210, a front detection slit 230, a rear detection slit 240, a front light amount sensor 252, a rear light amount sensor 254, and a calculating circuit 260 which is a example of calculating unit. The illumination optical system 200 has a light source 201, a beam expander 202, a dividing lens 204, a rotational phase plate 206, a collimator lens 208, and an illumination lens 212. In the level detection apparatus 100, an optical system is constructed by using the illumination optical system 200, the polarizing beam splitter 214, the wavelength $\lambda/4$ plate 216, the objective lens 218, the focusing lens 220, and the beam splitter 222. The optical system illuminates a surface of an target object 101 by illumination light 104 passing through the illumination slit 210 and focuses reflected light from the surface of the target object 101. The details will be described below.

Light 102 emitted from the light source 201 is expanded by the beam expander 202 to cause the dividing lens 204 to generate a surface light source. Thereafter, the light is caused to pass through the rotational phase plate 206 to reduce spatial coherency. Thereafter, a Fourier surface of the surface light source is generated by the collimator lens 208 to install the illumination slit 210 at a position of the Fourier surface. The light 102 passing through the illumination slit 210 is focused on the surface of the target object 101 by the illumination lens 212 and the objective lens 218. The illumination optical system 200 uniformly illuminates the surface of the target object 101 by a combination of the light 102 emitted from the light source 201 and the objective lens 218. The lens system is arranged such that the illumination slit 210 and the surface of the target object 101 are conjugated. The illumination light 104 passing through the illumination slit 210 is guided to the surface side of the target object 101 by the polarizing beam splitter 214. More specifically, the polarizing beam splitter 214 introduces the illumination light 104 into an optical path. The $\lambda/4$ plate 216 is arranged on the surface side of the target object 101 with respect to the polarizing beam splitter 214. The polarizing beam splitter 214 and the $\lambda/4$ plate 216 circularly polarizes light being incident on the surface of the target object 101. With this configuration, the illumination light 104 reflected by the target object 101 can be guided to a focusing system without loss. In this case, the polarizing beam splitter 214 and the $\lambda/4$ plate 216 are arranged immediately before the objective lens 218. However, the arrangement position of the polarizing beam splitter 214 is not limited to this position. The polarizing beam splitter 214 may be arranged at any position which is back of the illumination slit 210.

The objective lens 218 which illuminates the target object 101 by the illumination light 104 converges reflected light from the target object 101. The illumination light 104 reflected by the surface of the target object 101 passes through the objective lens 218, the $\lambda/4$ plate 216, and the polarizing beam splitter 214, and is focused by the focusing lens 220. In this manner, the focusing lens 220 forms an image of the target object 101 in combination with the focusing lens 220. In back of the focusing lens 220, the beam splitter 222 is arranged to split a reflected beam into two beams. In FIG. 1, a focal image optical system is constituted by the focusing lens 220 and the beam splitter 222. The focal image optical system is not limited to this system, and may be constructed by using another lens, a mirror, and the like.

In front of a focal point of one beam 106 of the split beams, the front detection slit 230 is arranged. In back of the front detection slit 230, the front light amount sensor 252 for detection is arranged. The front light amount sensor 252 detects an amount of light of the reflected beam 106 passing through the front detection slit 230. In back of the focal point of the other beam 108 of the split beams, the rear detection slit 240 is arranged. In back of the rear detection slit 240, the rear light amount sensor 254 for detection is arranged. The rear light amount sensor 254 detects an amount of light of the reflected beam 108 passing through the rear detection slit 240.

The calculating circuit 260 calculates a level (a position of the z direction, or "a height position of the z direction") of the surface of the target object 101 on the basis of outputs from the light amount sensors 252 and 254. More specifically, by using a level signal z of the surface of the target object 101, an output A from the front light amount sensor 252, an output B from the rear light amount sensor 254, and a proportionality constant k, the level of the surface of the target object 101 can be calculated by the following equation (1):

$$z = k \cdot (A-B)/(A+B) \qquad (1)$$

As expressed in Equation (1), when a difference between the outputs from the light amount sensors 252 and 254 is divided by a sum of the outputs, the level of the target object 101 can be calculated. A detected result is output outside the apparatus or to a monitor or the like.

Figure 2:
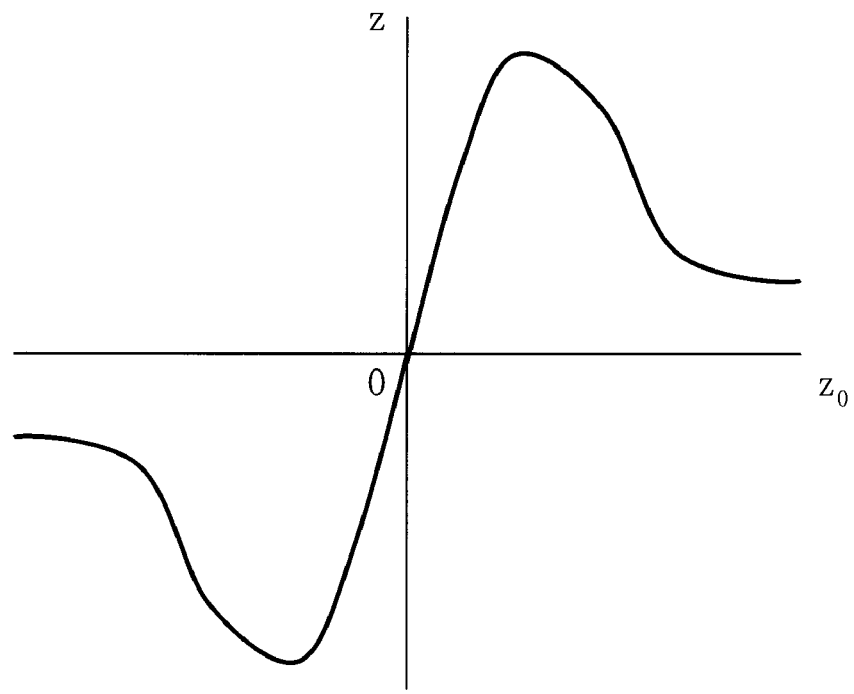
FIG. 2 is a graph showing a relationship between a level signal z and an actual level of a target object surface in the first embodiment.

FIG. 2 is a graph showing a relationship between a level signal z and an actual level $z_0$ of a target object surface in the first embodiment.

As shown in FIG. 2, with respect to the relationship between both the level signal and the level, linearity can be secured at almost zero. Therefore, positional detection is performed in a linear region to make it possible to calculate the level by primary proportionality relation. As a result, accurate level detection can be performed.

Figure 3:
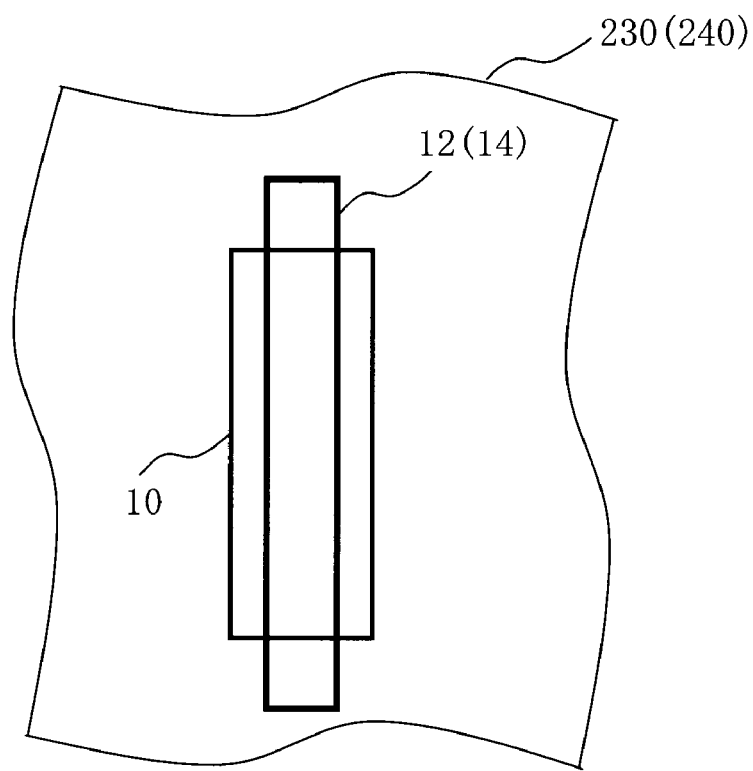
FIG. 3 is a diagram showing an example of a relationship between an illumination slit image and a detection slit in the first embodiment.

FIG. 3 is a diagram showing an example of a relationship between an illumination slit image and a detection slit in the first embodiment.

In the illumination slit 210, a rectangular opening (first opening) which causes the illumination light 104 to pass is formed. FIG. 3 shows an illumination slit image 10 formed through the opening. In this case, in the front detection slit 230, an opening 12 (second opening) is formed to have a rectangular shape the short side of which is shorter than the short side of the illumination slit image 10 and the long side of which is longer than the long side of the illumination slit image 10. Similarly, in the rear detection slit 240, an opening 14 (second opening) is formed to have a rectangular shape the short side of which is shorter than the short side of the illumination slit image 10 and the long side of which is longer than the long side of the illumination slit image 10. The openings 12 and 14 are formed to have the same shapes. In this manner, one of the vertical and horizontal sides of the opening is made shorter than the corresponding side of the illumination slit image 10 to regulate an amount of passing light, so that detection can be performed depending on motion of the level position z of the target object 101. On the other hand, the side of the opening is make larger than the corresponding side of the illumination slit image 10 to made amounts of passing light in the direction of the large side in front of and in back of the focal point equal to each other.

FIGS. 4A and 4B are diagrams showing an example obtained by comparing a circular pin hole and a rectangular slit when a target object surface having a reflectance distribution is illuminated.

FIGS. 5A and 5B are diagrams showing an example obtained by comparing a case in which an illumination image in front of a focal point of a target object surface having a reflectance distribution passes through the circular pin hole with a case in which the illumination image passes through the rectangular slit.

Figures 6A, 6B:
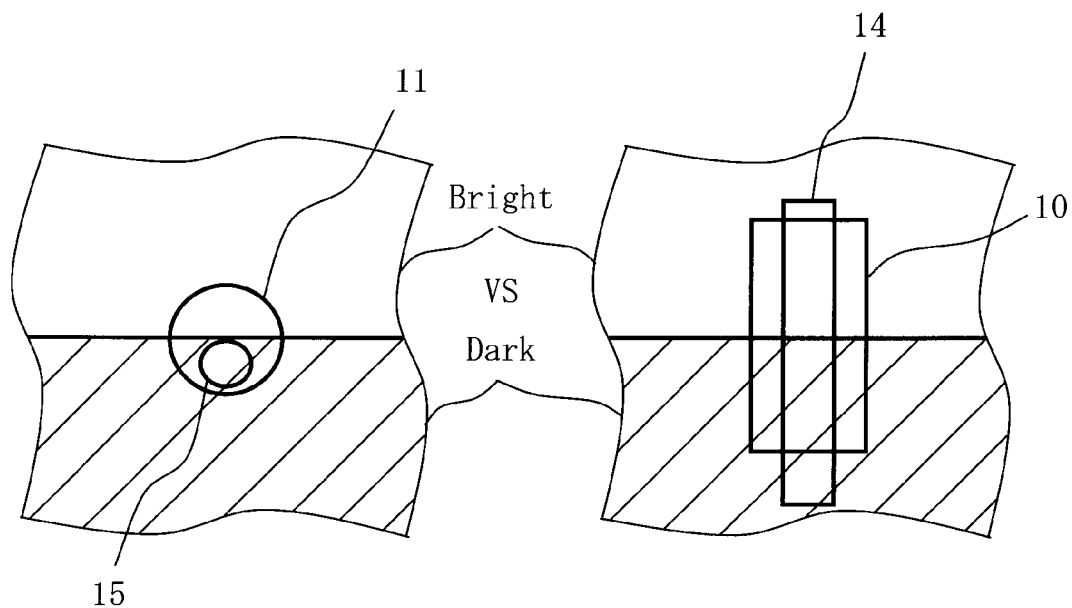
FIGS. 6A and 6B are diagrams showing an example obtained by comparing a case in which an illumination image in back of a focal point of a target object surface having a reflectance distribution passes through the circular pin hole with a case in which the illumination image passes through the rectangular slit.

FIGS. 6A and 6B are diagrams showing an example obtained by comparing a case in which an illumination image in back of a focal point of a target object surface having a reflectance distribution passes through the circular pin hole with a case in which the illumination image passes through the rectangular slit.

When a boundary portion between a bright portion and a dark portion on a target object surface as shown in FIG. 4A is irradiated with illumination light 17 passing through a circular pin hole, as shown in FIG. 5A, a circular pin hole 13 in front of the focal point may cause only the bright portion of an illumination pin hole image 11 to pass. At the same time, as shown in FIG. 6A, a circular pin hole 15 in back of the focal point may cause only the dark portion of the illumination pin hole image 11 to pass. In this case, a change in amount of light caused by an error of the installation positions of the circular pin holes 13 and 15 but an originally desired change in amount of light at the positions in front of and in back of the focal point is naturally detected. In this case, even though the amounts of light passing through the circular pin holes in front of and in back of the focal point are measured, a level position to be detected has an error. On the other hand, when the rectangular slit according to the first embodiment is used, this problem is solved as follows. When a boundary portion between a dark portion and a bright portion on the target object surface as shown in FIG. 4B is irradiated by illumination light 16 passing through the rectangular slit, as shown in FIG. 5B, even if the position of the rectangular opening 12 of the detection slit 230 in front of the focal point shifts in a direction (upper side) perpendicular to the boundary, an amount of passing light including the illumination slit image 10 does not change. Similarly, as shown in FIG. 6B, even if the position of the rectangular opening 14 of the detection slit 240 in back of the focal point shifts in a direction (lower side) perpendicular to the boundary, an amount of passing light including the illumination slit image 10 does not change. Accordingly, a change in amount of light caused by an error of the installation positions of the detection slits 230 and 240 in a direction perpendicular to the boundary can be suppressed. Therefore, a desired change in amount of light in front of and in back of the focal point can be measured.

Figures 7A, 7B:
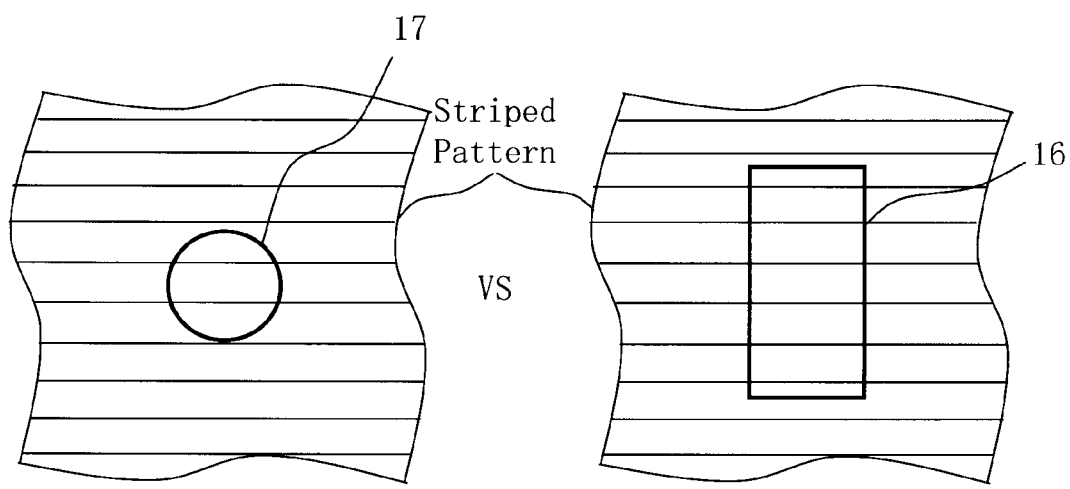
FIGS. 7A and 7b are diagrams showing an example obtained by comparing a circular pin hole with a rectangular slit when a target object surface having a striped pattern is illuminated.

FIGS. 7A and 7B are diagrams showing an example obtained by comparing a circular pin hole with a rectangular slit when a target object surface having a striped pattern is illuminated.

FIGS. 8A and 8B are diagrams showing an example obtained by comparing a case in which an illumination image in front of a focal point of the target object surface having the striped pattern passes through the circular pin hole with a case in which the illumination image passes through the rectangular slit.

FIGS. 9A and 9B are diagrams showing an example obtained by comparing a case in which an illumination image in back of the focal point of the target object surface having the striped pattern passes through the circular pin hole with a case in which the illumination image passes through the rectangular slit.

When a pattern portion of the striped pattern of the target object surface as shown in FIG. 7A is illuminated by the illumination light 17 passing through the circular pin hole, as shown in FIG. 8A, in addition to the illumination pin hole image 11, images 19 and 21 may be generated by diffracted light. At this time, the circular pin hole 13 in front of the focal point may cause all beams of the illumination pin hole image 11 and the images 19 and 21 obtained by the diffracted light to pass. On the other hand, at the same time, as shown in FIG. 9A, the circular pin hole 15 in back of the focal point may cause only beams of the illumination pin hole image 11 and the image 21 obtained by the diffracted light to pass to misalign a beam of the image 19 obtained by the diffracted light. In this case, a change in amount of light caused by an error of the installation positions between the circular pin holes 13 and 15 but an originally desired change in amount of light at positions in front of and in back of the focal point is naturally detected. In this case, even though amounts of light passing through the circular pin holes in front of and in back of the focal point are measured, a level position to be detected has an error. On the other hand, when the rectangular slit according to the first embodiment is used, this problem is solved as follows. When a pattern portion of a striped pattern on the target object surface as shown in FIG. 7B is irradiated by the illumination light 16 passing through the rectangular slit, as shown in FIG. 8B, even if the position of the rectangular opening 12 of the front detection slit 230 in front of the focal point is misaligned in a direction (upper side) perpendicular to a straight line of the striped pattern, amounts of passing light of the illumination slit image 10 and images 18 and 24 obtained by diffracted light do not change. Similarly, as shown in FIG. 9B, even if the position of the rectangular opening 14 of the rear detection slit 240 in back of the focal point is misaligned in a direction (lower side) perpendicular to the straight line of the striped pattern, amounts of passing light of the illumination slit image 10 and the images 18 and 24 obtained by diffracted light do not change. For this reason, a change in amount of light caused by an error of the installation positions between the detection slits 230 and 240 in the direction perpendicular to the straight line of the striped pattern can be suppressed. Thereafter, an originally desired change in amount of light at positions in front of and in back of the focal point can be measured.

As described above, according to the embodiment, an error caused by an influence of a reflectance distribution and an error caused by diffracted light can be reduced.

Second Embodiment

In the first embodiment, since one rectangular illumination slit 210 and the detection slits 230 and 240 are used, when the longitudinal direction of the rectangle is the direction perpendicular to the boundary between the reflectance distributions, an effect can be obtained. However, the direction of the boundary of the reflectance distributions of the pattern in the target object is not limited to one direction. Similarly, the direction of the pattern of the striped pattern which generates diffracted light is not always one direction. Therefore, in a second embodiment, a case in which the illumination slit 210 and the detection slits 230 and 240 have a plurality of openings will be described below. The configurations of the opening of the illumination slit 210 and the openings of the detection slits 230 and 240 except for the shapes thereof are the same as those of the first embodiment.

Figure 10:
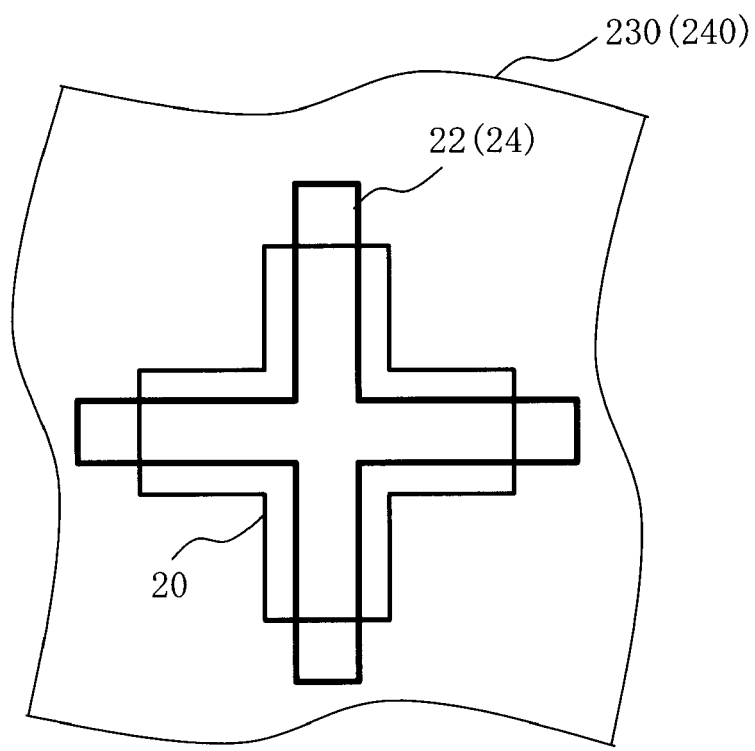
FIG. 10 is a diagram showing an example of a relationship between an illumination slit image and a detection slit in a second embodiment.

FIG. 10 is a diagram showing an example of a relationship between an illumination slit image and a detection slit in the second embodiment.

In the illumination slit 210, an opening (first opening) is formed such that two rectangles are crisscross combined at an angle of 90° to have perpendicular longitudinal directions, so that an illumination slit image 20 as shown in FIG. 10 is formed when illumination light 104 is caused to pass through the opening. In this case, the two rectangles are combined to cross at a central position of the opening. As in the detection slits 230 and 240, each of openings 22 and 24 (second opening) is formed such that two rectangles are crisscross combined at an angle of 90° at the central position of the opening to have perpendicular longitudinal directions. The openings 22 and 24 are formed to have the same shapes. However, in the opening 22 of the detection slit 230, the two rectangles are combined such that a short side of the rectangle is shorter than a short side of the illumination slit image 20 and such that a long side of the rectangle is longer than the long side of the illumination slit image 20. Similarly, also in the opening 24 of the detection slit 240, the two rectangles are combined such that a short side of the rectangle is shorter than a short side of the illumination slit image 20 and such that a long side of the rectangle is longer than the long side of the illumination slit image 20. In this manner, the plurality of openings are formed to have shapes obtained by combining the openings in directions having different angles to average the influences on the target object 101, so that an error can be reduced. However, the openings are not limited to the above shapes, and the openings suitably have the following shapes.

Figure 11:
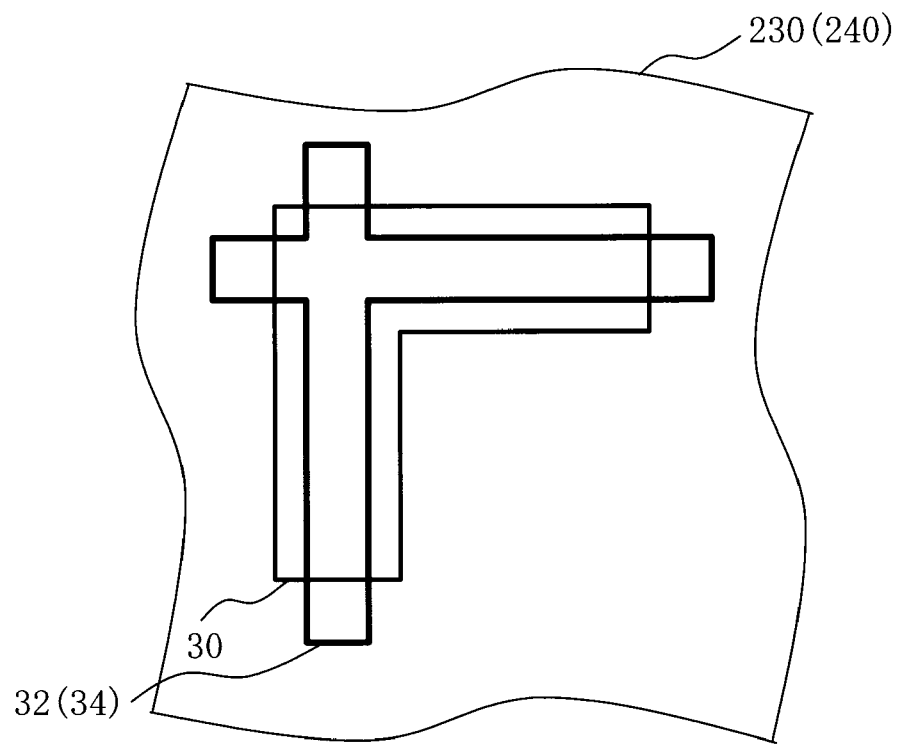
FIG. 11 is a diagram showing another example of the relationship between the illumination slit image and the detection slit in the second embodiment.

FIG. 11 is a diagram showing another example of the relationship between the illumination slit image and the detection slit in the second embodiment.

In the illumination slit 210, an opening (first opening) is formed such that two rectangles are crisscross combined at an angle of 90° to have perpendicular longitudinal directions, so that an illumination slit image 30 as shown in FIG. 11 is formed when illumination light 104 is caused to pass through the opening. In this case, the two rectangles are combined to cross near an end portion of the opening. As in the detection slits 230 and 240, each of openings 32 and 34 (second opening) is formed such that two rectangles are crisscross combined at an angle of 90° near an end portion of the opening to have perpendicular longitudinal directions. The openings 32 and 34 are formed to have the same shapes. However, in the opening 32 of the detection slit 230, the two rectangles are combined such that a short side of the rectangle is shorter than a short side of the illumination slit image 30 and such that a long side of the rectangle is longer than the long side of the illumination slit image 30. Similarly, also in the image 34 of the detection slit 240, the two rectangles are combined such that a short side of the rectangle is shorter than a short side of the illumination slit image 30 and such that a long side of the rectangle is longer than the long side of the illumination slit image 30. In this manner, the rectangles need not be caused to cross at the central position of the slit opening, and, as shown in FIG. 11, the rectangles may be caused to cross at a different position, for example, near an end portion. Furthermore, the following shape maybe suitably used.

Figure 12:
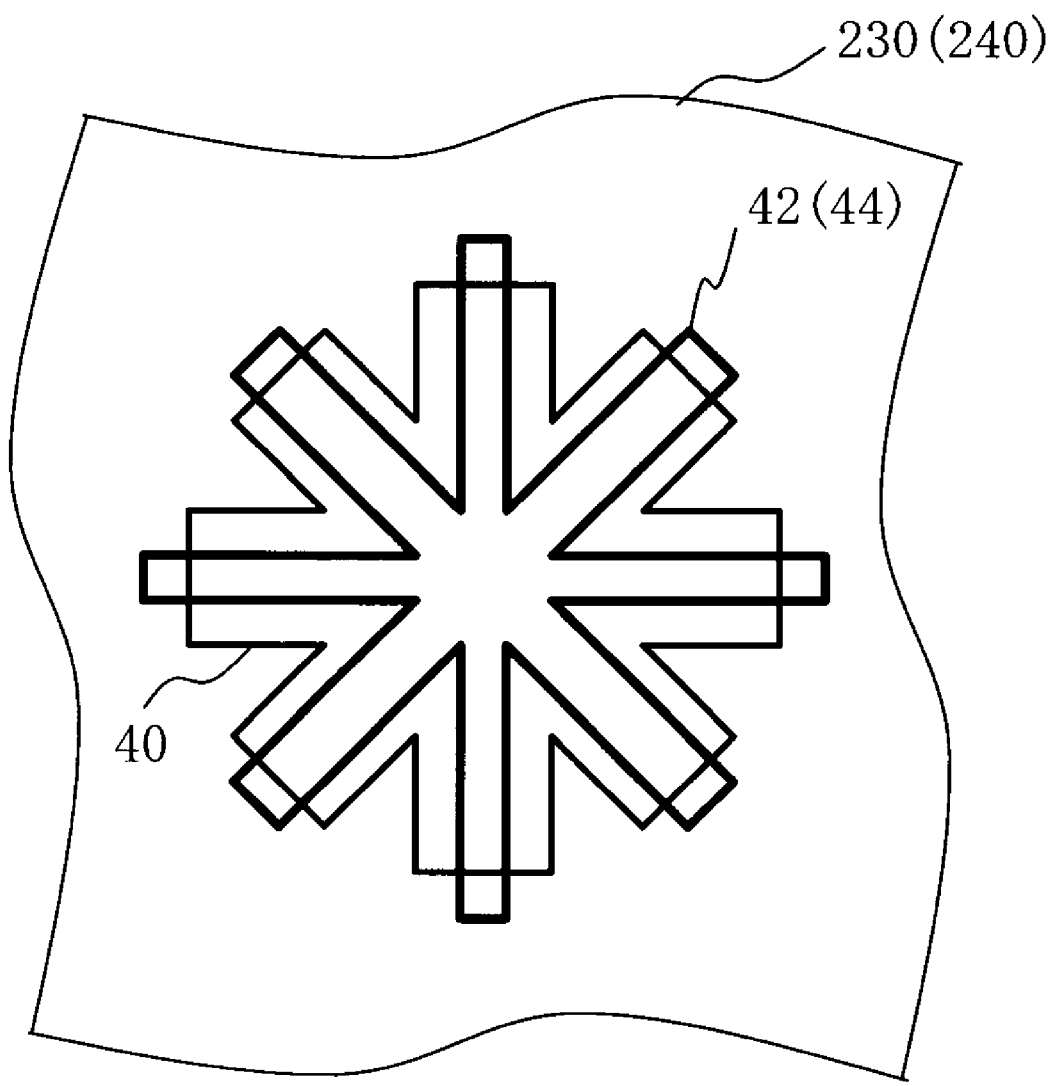
FIG. 12 is a diagram showing still another example of the relationship between the illumination slit image and the detection slit in the second embodiment.

FIG. 12 is a diagram showing still another example of the relationship between the illumination slit image and the detection slit in the second embodiment.

In the illumination slit 210, an opening (first opening) formed such that four rectangles are shifted every 45° to have an asterisk shape, so that an illumination slit 40 as shown in FIG. 12 is formed when the illumination light 104 is caused to pass through the opening. In this case, the opening has the shape which is formed such that the four rectangles are shifted at the predetermined angle and crisscrossed at the center of the opening. As in the detection slits 230 and 240, four rectangles are crisscross shifted every 45° at the center of the opening to form each of openings 42 and 44 (second openings). The openings 42 and 44 are formed to have the same shapes. However, in the opening 42 of the detection slit 230, the four rectangles are combined such that a short side of the rectangle is shorter than a short side of the illumination slit image 40 and such that a long side of the rectangle is longer than the long side of the illumination slit image 40. Similarly, also in the image 44 of the detection slit 240, the four rectangles are combined such that a short side of the rectangle is shorter than a short side of the illumination slit image 40 and such that a long side of the rectangle is longer than the long side of the illumination slit image 40. In this manner, furthermore, the rectangles extending at different angles are combined to make it possible to further average influence of the target object 101 and to further reduce an error.

Each of FIGS. 10 to 12 described above is only an example. The present invention is not limited to these examples. When a plurality of rectangles each of which has a short side shorter than the short side of the illumination slit image and a long side longer than the long side of the illumination slit image, other shapes may be employed.

Third Embodiment

Although each of the plurality of slit openings has a crisscross shape, a plurality of rectangles having different directions are not always required at the same time. A shape of the slit opening may be selected as needed. Therefore, in the third embodiment, a configuration in which slit openings having a plurality of shapes are arranged and formed in an illumination slit and front and rear detection slit will be described below.

Figure 13:
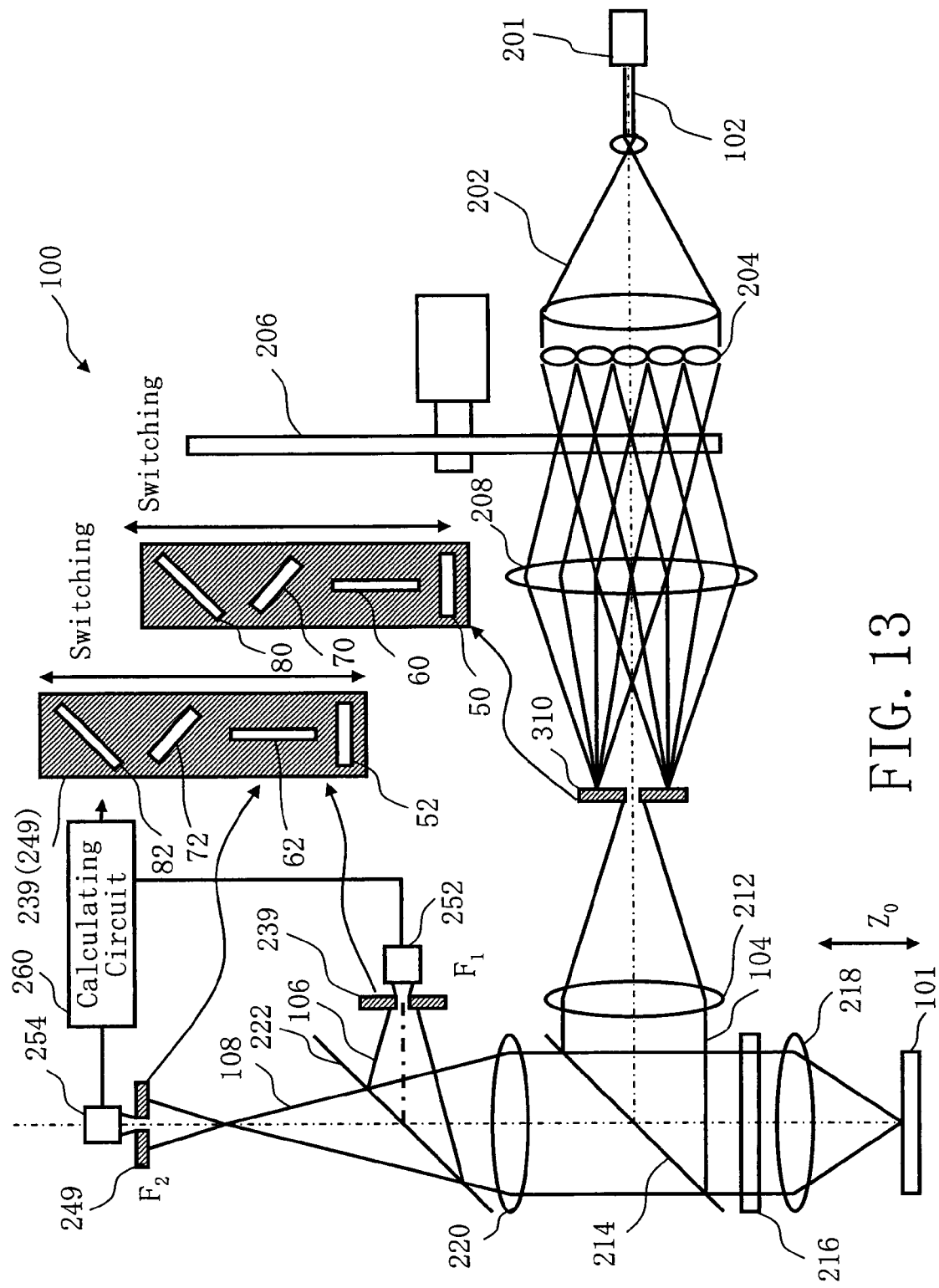
FIG. 13 is a conceptual diagram showing a configuration of a level detection apparatus according to a third embodiment.

FIG. 13 is a conceptual diagram showing a configuration of a level detection apparatus according to the third embodiment.

A level detection apparatus 100 in FIG. 3 has the same configuration as that in FIG. 1 except that a illumination slit 310 is used in place of the illumination slit 210, a detection slit 239 is used in place of the detection slit 230, and a detection slit 249 is used in place of the detection slit 240. In the illumination slit 310, a rectangular opening 50 which is long in a lateral direction (horizontal direction), a rectangular opening 60 which is long on upper and lower sides (vertical direction or direction of height), a rectangular opening 70 which is long on the diagonally upper left shifted at 45°, and a rectangular opening 80 which is long on the diagonally upper right which is shifted at 45° are formed. In the detection slits 239 and 249 also, a rectangular opening 52 which is long in a lateral direction (horizontal direction), a rectangular opening 62 which is long on upper and lower sides (vertical direction or direction of height), a rectangular opening 72 which is long on the diagonally upper left shifted at 45°, and a rectangular opening 82 which is long on the diagonally upper right shifted at 45° are formed. However, as described above, each opening of the detection slits 239 and 249 is formed such that the short side of the rectangle is shorter than the short side of the illumination slit image and such that the long side is longer than the long side of the illumination slit image. The openings of the detection slits 239 and 249 are formed to have the same shapes. The illumination slit 210 and the detection slits 239 and 249 are synchronously switched such that slit openings having the same direction are arranged in an optical path. For example, suitably, the slits may be manually switched or driven by a pulse motor or the like or may be switched and inserted into the optical path. When the switching operation is synchronously performed, the switching operation may be performed even during detection of a level, or the slits may be switched for every target object 101.

With the above configuration, a level can be detected in a more appropriate slit shape depending on a pattern.

Fourth Embodiment

In the third embodiment, the configuration in which the slit openings having a plurality of shapes are arranged and formed is described. In a fourth embodiment, a configuration in which a direction is changed by using one slit opening will be described below.

Figure 14:
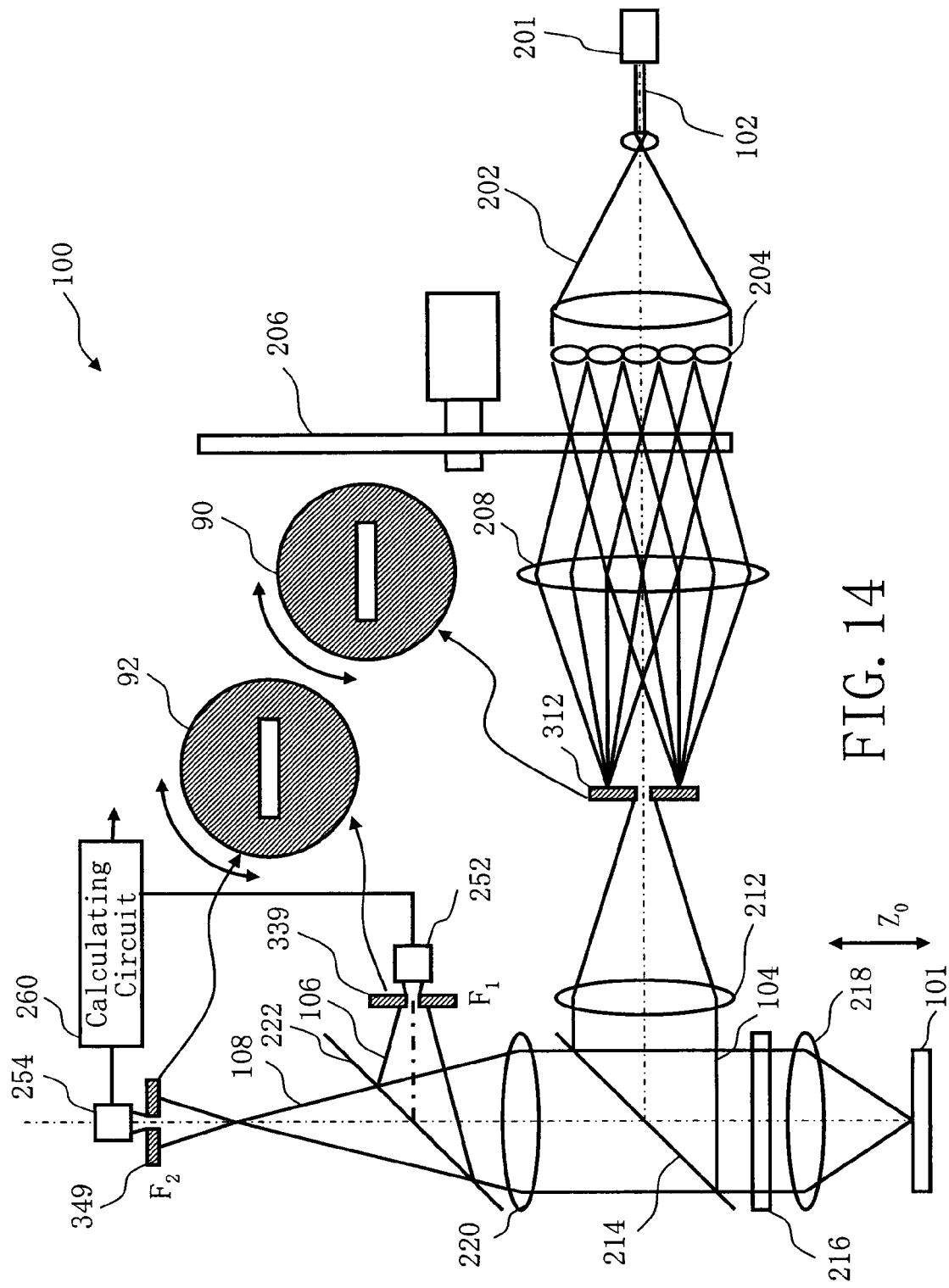
FIG. 14 is a conceptual diagram showing a configuration of a level detection apparatus according to a fourth embodiment.

FIG. 14 is a conceptual diagram showing a configuration of a level detection apparatus according to the fourth embodiment.

A level detection apparatus 100 in FIG. 14 has the same configuration as that in FIG. 1 except that an illumination slit 312 is used in place of the illumination slit 210, a detection slit 339 is used in place of the detection slit 230, and a detection slit 349 is used in place of the detection slit 240. In the illumination slit 312, a rectangular opening 90 which is long in a lateral direction (horizontal direction) is formed. In the detection slits 339 and 349 also, a rectangular opening 92 which is long in a lateral direction (horizontal direction) is formed. However, as described above, the openings 92 of the detection slits 339 and 349 are formed such that the short side of the rectangle is shorter than a short side of an illumination slit image to be obtained and the long side is longer than the long side of the illumination slit image. The openings 92 of the detection slits 339 and 349 are formed to have the same shapes. The illumination slit 312 and the detection slits 339 and 349 synchronously rotate such that slit openings having the same direction are arranged in an optical path. For example, suitably, the slits may be manually rotated or driven by a pulse motor or the like to be rotated in the optical path. When the rotating operations are synchronously performed, the rotating operations may be performed during detection of a level, or the rotating operations may be switched for every target object 101. A direction of the slit opening may be selected as needed. Alternatively, the slit openings may always rotate. When the slit openings are always rotated, as in the second embodiment, influence of the target object 101 is averaged to make it possible to reduce an error.

The embodiments will be described below with reference to the concrete examples. However, the present invention is not limited to these concrete examples.

Although the level detection apparatus explained in each of the embodiment uses reflected light, transmitted light may be used. The level detection apparatus may be used in a pattern inspection apparatus to inspect a defect of a lithography mask used when a semiconductor device or a liquid crystal display (LCD) is manufactured. The pattern inspection apparatus used at this time may be a die to database inspection apparatus which generates a reference image serving as inspection reference pattern data and a die to die inspection apparatus which uses data of the same pattern the image of which is picked by a sensor such as a photodiode array. The pattern inspection apparatus may be an apparatus for performing inspection by using transmitted light and an apparatus for performing inspection by using reflected light or using transmitted light and the reflected light simultaneously.

Parts such as an apparatus configuration and a control method which are not directly required for the explanation of the present invention are omitted. However, a necessary apparatus configuration or a necessary control method may be arbitrarily used.

In addition, all level detection apparatuses and pattern inspection apparatuses which include the elements of the present invention and the designs of which can be arbitrarily changed by a person skilled in the art are included in the scope of the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A level detection apparatus comprising:
   an illumination slit in which a rectangular first opening which causes illumination light to pass is formed;
   an optical system configured to illuminate a target object surface by illumination light passing through the illumination slit and focuses reflected light from the target object surface;
   first and second detection slits which are arranged in front of and in back of a focal point and in each of which a second opening is formed such that a short side of a rectangle is shorter than a short side of a illumination slit image formed by the illumination slit and a long side of the rectangle is larger than a long side of the illumination slit image;
   first and second light amount sensors configured to detect amounts of light of the reflected lights passing through the first and second detection slits; and
   a calculating unit configured to calculate a level of the target object surface based on outputs from the first and second light amount sensors.

2. The level detection apparatus according to claim 1, wherein the optical system includes:
   a polarizing beam splitter which guides illumination light to the target object surface side; and
   an ¼ wavelength plate arranged on the target object surface side with respect to the polarizing beam splitter.

3. The level detection apparatus according to claim 1, wherein the illumination slit is formed in a shape which is obtained such that a plurality of the first openings are combined to each other to have directions at different angles, and
   the first and second detection slits are formed in shapes each of which is obtained such that a plurality of the second openings are combined with each other to have directions at different angles.

4. The level detection apparatus according to claim 3, wherein the illumination slit is formed in a shape which is obtained such that two of the first openings are combined with each other to have longitudinal directions perpendicular to each other, and the first and second detection slits are formed in shapes each of which is obtained such that two of the second openings are combined with each other to have longitudinal directions perpendicular to each other.

5. The level detection apparatus according to claim 3, wherein the illumination slit is formed in a shape which is obtained such that four of the first openings are combined with each other to be shifted from each other at 45°, and the first and second detection slits are formed in shapes each of which is obtained such that four of the second openings are combined to each other to be shifted from each other at 45°.

6. The level detection apparatus according to claim 1, wherein the directions of the first and second openings are synchronously switched.

7. The level detection apparatus according to claim 1, further comprising a beam splitter which splits the reflected light passing through the first and second detection slits.

8. The level detection apparatus according to claim 7, wherein the first light amount sensor detects an amount of light of one of the split reflected lights, and the second light amount sensor detects an amount of light of the other of the split reflected lights.

9. The level detection apparatus according to claim 1, wherein the illumination slit is formed in a shape which is obtained such that a plurality of the first openings having different angles do not overlap, and the first and second detection slits are formed in shapes each of which is obtained such that a plurality of the second openings having different angles do not overlap.

10. The level detection apparatus according to claim 9, wherein the illumination slit and the first and second detection slits are switched such that the first and second openings having the same directions are arranged in an optical path.

* * * * *